United States Patent [19]

Tokuyama et al.

[11] 4,364,985
[45] Dec. 21, 1982

[54] POROUS SHEET

[75] Inventors: Mitsuru Tokuyama, Utsunomiya; Kenji Ohki, Chiba; Masayuki Sagae, Tochigi; Kaoru Tsujii, Utsunomiya, all of Japan

[73] Assignee: Kao Soap Co., Ltd., Tokyo, Japan

[21] Appl. No.: 268,204

[22] Filed: May 29, 1981

[30] Foreign Application Priority Data

May 29, 1980 [JP] Japan ............................. 55-71864

[51] Int. Cl.³ ..................... B32B 5/16; B32B 27/14
[52] U.S. Cl. .............................. 428/149; 51/281 R; 264/239; 264/340; 428/143; 428/323; 428/325; 428/327; 428/330; 428/331; 428/332
[58] Field of Search ............. 428/323, 325, 327, 329, 428/330, 331, 155, 332, 143, 149, 904, 913, 403; 51/293, 296, 281 R; 264/239, 340

[56] References Cited

U.S. PATENT DOCUMENTS 3,154,461 10/1964 Johnson ............................. 428/323
3,906,684 9/1975 Marshall et al. ..................... 51/296
4,020,211 4/1977 Eigenmann ........................ 428/323

OTHER PUBLICATIONS

"Cultured Stones", *SPE Journal*, Aug. 1966, pp. 36–39.

*Primary Examiner*—Paul J. Thibodeau
*Attorney, Agent, or Firm*—Flynn, Thiel, Boutell & Tanis

[57] ABSTRACT

A porous sheet is disclosed that comprises a thin, flexible sheet made of thermoplastic resin having solid particles distributed therein. Small spaces are formed around the particles, such that abrasion or buffing of the opposite surfaces of the sheet causes the formation of a multitude of fine pores that extend through the sheet, making the sheet vapor-permeable but liquid-impermeable.

10 Claims, 7 Drawing Figures

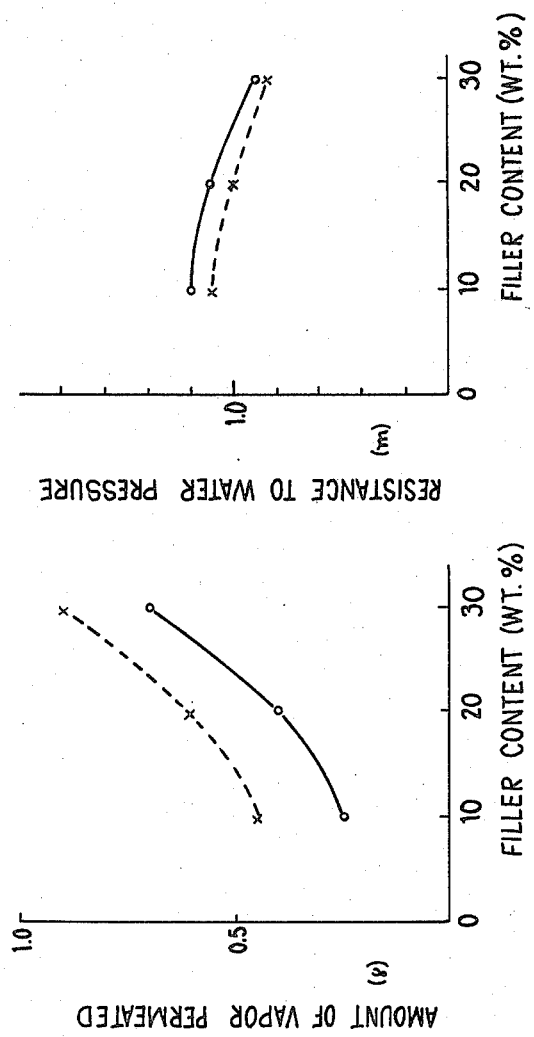

POROUS SHEET

The present invention relates to a porous sheet. More particularly, the present invention relates to a porous sheet impermeable to liquid but permeable to vapor.

Porous sheets impermeable to liquid but permeable to vapor have been used in various fields such as the fields of hygienic materials, medical science, food industry, cosmetics and clothes. The porous sheet of the present invention is usable in all of the above fields. The present invention will be described below with reference to disposable diapers.

Recently, the use of disposable diapers for babies has gradually spread. The disposable diapers now available on the market are easier to use and more comfortable than cloth diapers. However, there still remain some problems to be solved. There is observed a phenomenon that babies have skin eruptions due to the diapers, though this phenomenon is not a defect of only disposable diapers. The improvement on this point has eagerly been demanded. It is considered that the eruption of the skin is caused by the use of a material impermeable to liquid as the outer layer, i.e. back sheet, of the disposable diaper in order to inhibit the penetration of the liquid through the back sheet and to prevent staining of the surroundings. The impermeability to liquid is indispensable as a function of diapers as a matter of course. For the prevention of the eruption of the skin, it is desirable to employ a back sheet permeable to vapor. These properties are obtained generally by using porous sheets having numerous fine pores. The porous sheets are currently produced by a process wherein pores are provided in a film by electric discharge, a process wherein a film containing a filler is stretched or a process wherein a filler is removed from a film containing the filler. However, the sheets obtained by those processes are still unsuitable for use in disposable diapers because of their high costs or insufficient strength.

Therefore, the object of the present invention is to provide a porous sheet impermeable to liquid and permeable to vapor which has a high strength and which can be produced easily at low cost and can be used for the preparation of disposable products.

The porous sheet of the present invention is characterized in that the sheet is obtained by the abrasion or buffing of the surface of a thermoplastic, flexible sheet containing solid particles so that the particles are exposed onto the flexible sheet surface. The present invention will now be described in detail.

BRIEF DESCRIPTION OF DRAWINGS

FIGS. 6-A and 6-B are graphs showing the amount of vapor permeation and water pressure resistance properties of the porous sheets obtained in Example 1.

Figure 1:
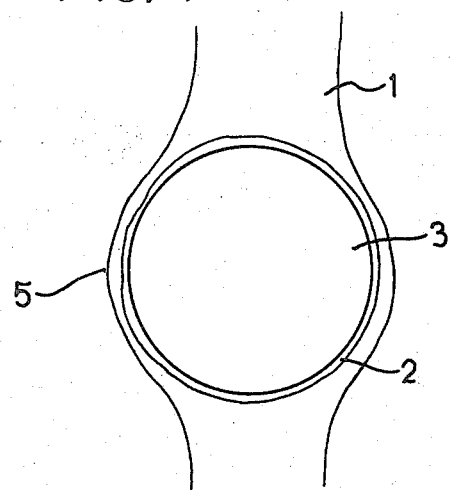
FIG. 1 is an enlarged partial cross section showing an embodiment of a filler-containing sheet used in the present invention.
Figure 2:
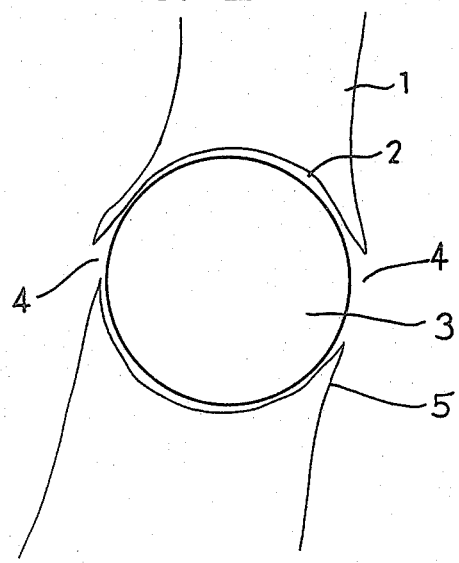
FIG. 2 is an enlarged partial cross section of a porous sheet of the present invention obtained by the abrasion or buffing of the sheet shown in FIG. 1.

The reference numerals of the drawings identify the following elements:
1—Thermoplastic material
3—Filler
5—Flexible sheet
6,7—Rollers
8,9,10,11—Abrasive rolls Sheets containing solid particles (hereinafter referred to as filler) have been well known. In the production of a porous sheet by a stretching method, a thermoplastic film is stretched to enlarge the cavities between the filler particles and the film. However, in the porous sheet produced by this method, the longitudinal strength is not well-balanced with the transverse strength. The thermoplastic, flexible sheet containing the filler according to the invention is prepared by incorporating the filler in a molten, thermoplastic material, shaping the same in the form of a film and cooling the film. Accordingly, an aperture 2 forming the boundary between the thermoplastic material 1 and the filler 3 is formed, due to the difference in thermal expansion coefficient between them, as shown in the cross section of the thermoplastic flexible sheet in FIG. 1. If the surface and the back of a filler-containing, thermoplastic flexible sheet is abraded or buffed, taking advantage of the aperture 2, part of the filler particle 3 is exposed on the opposite surfaces of the flexible sheet 5 as shown by 4 in FIG. 2. Thus, the aperture 2 between the thermoplastic material 1 and the filler particle 3 penetrates through the flexible sheet 5 (from the front surface to the back surface) to make the flexible sheet 5 porous. The openings formed by the apertures 2 are very fine and generally they are impermeable to liquid and permeable to vapor. If there is a fear of liquid leakage due to the size of the openings 2, which depends on the thermoplastic material 1 or filler 3 used, the object can be attained by treating the filler 3 to impart water-repellency thereto.

The thermoplastic, flexible sheets used in the present invention are those whose volume is reduced when the sheets are formed from the molten material and which can easily be folded and bent. For example, they include polyethylene, nylon and polypropylene films. The solid particles (fillers) used in the present invention are those compatible with the molten thermoplastic material while the particles are kept in the form of solid and which can be incorporated in the flexible sheet. As the fillers, there may be mentioned, for example, glass beads, polystyrene, silica, calcium carbonate, barium sulfate, silica alumina gel, pearlite, diatomaceous earth, zeolite and white carbon. The shape of the fillers is not necessarily spherical, and needle-shaped, porous or hollow fillers may also be used. From the viewpoint of easiness of the preparation of the filler-containing, flexible sheet, the diameter of the filler particles is preferably in the range of from 1 micron to the thickness of the flexible sheet plus 60 microns. The term "size of the filler" herein indicates not only the size of the primary particles but also the sizes of grains thereof such as secondary particles each comprising a mass of plural primary particles. For the effective use of the filler having a particle size of near to the lower limit in the above range, it is necessary to arrange the filler particles in layers in the flexible sheet. The shape of the filler is not limited to the spherical and, therefore, the term "diameter" herein indicates the so-called equivalent diameter, i.e. the cube root of a value given by dividing the filler volume by $\pi/6$. When a hydrophilic substance such as glass beads or silica is used as the filler, the resulting sheet has a poor water resistance. In such a case, the porous sheet or polytetrafluoroethylene resin sold under trademark the filler is treated with a water-repelling substance such as a silicon emulsion or Teflon (DuPont) to impart water-repellency to the porous sheet. This treatment can be effected by a known method such as the spray method or immersion method.

It is preferred that the amount of the filler particles ranges from 5 wt.% to 40 wt.%, especially from 5 wt.% to 30 wt.%, based on the total weight of said particles and the sheet.

Figure 3:
FIG. 3 is a photomicrograph of a cross section of a filler-containing sheet used in the present invention.
Figure 4:
FIG. 4 is a photomicrograph of the surface of a porous sheet of the present invention obtained in Example 1.

For easy understanding of the present invention, photomicrographs of the porous sheets of the present invention are shown in FIGS. 3 and 4. FIG. 3 is a photomicrograph of a section of a low density polyethylene sheet in which 30–40μ glass beads have been incorporated as the filler. Apertures formed between the glass bead and polyethylene are clearly shown. FIG. 4 is a photomicrograph of the surface of a porous sheet prepared in Example 1 given below. From FIG. 4, it is understood that the glass beads are exposed on the surface of the porous sheet, whereby the apertures function as the openings.

The porous sheet of the present invention is prepared by abrasion or buffing. The abrasion method has an advantage of a high preparation speed, since it is effected by the scraping of the sheet surface. The buffing method has an advantage of a fine finish, since it is effected by the wearing of the sheet surface.

Figure 5:
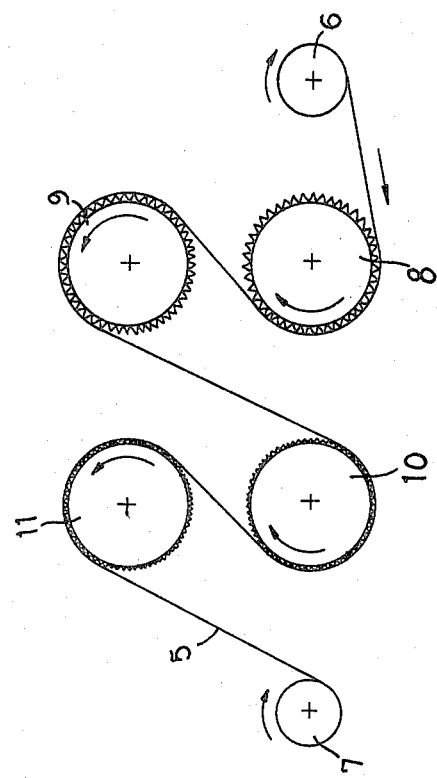
FIG. 5 is a flow sheet showing an embodiment of the abrasion device used for the production of a porous sheet of the present invention.

An embodiment of the process for the preparation of the porous sheet by abrasion according to the present invention is shown in FIG. 5. In FIG. 5, a sheet containing a filler is delivered by a delivery roller 6. The surface of the sheet is abraded by abrasive rolls 8 and 10 and the back thereof is abraded by abrasive rolls 9 and 11. The thus-obtained porous sheet 5 is reeled up by a wind-up roller 7. The abrasive rolls 8, 9, 10 and 11 rotate in the same direction as the running direction of the flexible sheet 5. The standard surface speed of those rolls is 10 times as high as the running speed of the plastic sheet. The surface speed of the abrasive rolls 10 and 11 is equal to or higher than the surface speed of the abrasive rolls 8 and 9. The abrasive surfaces of the rolls 8 and 9 are rougher than those of the rolls 10 and 11. The roughness of the abrasive surfaces is selected depending on the conditions of the plastic sheet 5, i.e. filler size and filler content of the sheet. For example, a roughness of AA 100–1000 according to JIS standard is preferred for the abrasion of a sheet having a thickness of 15–50 microns and containing 5–30 wt.% of a filler of an average particle diameter of 20–50 microns.

In the porous sheets of the present invention having the above described structures, the quantity of the vapor that permeates through the sheet can easily be controlled by altering the amount and size of the filler and the working conditions. As compared with porous sheets obtained by the conventional stretching method, the sheets of the present invention are characterized by a smaller reduction in strength and their well-balanced strength in machine direction and strength in cross direction.

The present invention will be illustrated by way of examples and referential examples, which by no means limit the invention. Unless otherwise stated, percentages are given by weight.

EXAMPLE 1

10 wt.%, 20 wt.% and 30 wt.% of glass beads having a diameter of 30–40μ, a specific gravity of 2.50 and a Mohs' hardness of 6.5 was kneaded in a low density polyethylene having a weight-average molecular weight of 9,300, a melt index of 5 and a melting point of 109° C. Films of a thickness of 30μ were prepared therefrom by the inflation method. The films were then made porous by means of the abrasion device shown in FIG. 5 under abrasion conditions No. 1 or No. 2 shown in following Table 1. The porous films were then treated in a 2% solution of a fluorine-containing water-repellent emulsion in such a manner that the water-repellent was attached thereto in an amount of 7%. The amount of vapor that permeated through the water-repellent, porous sheet and the resistance of the sheet to water pressure (JIS 1092) were measured to obtain the results shown in FIGS. 6-A and 6-B. In FIGS. 6-A and 6-B, the broken lines show the results of the sheets obtained under abrasion conditions No. 1 and the solid lines show the results of the sheets obtained under abrasion conditions No. 2.

The tests on the amount of permeated vapor were carried out as follows:

Tests on the Amount of Permeated Vapor 10 c.c. of distilled water was placed in a petri dish having a diameter of 90 mm and a height of 20 mm. The petri dish was covered with the porous sheet obtained in above Example 1, the periphery was sealed with a vinyl tape and the weight ($W_1$) was measured. The whole was allowed to stand in a constant temperature room at a temperature of 30° C. and a humidity of 65% for 2 hours. Thereafter, the weight thereof ($W_2$) was measured. The amount of permeated vapor (W) was calculated as follows:

$$W = W_1 - W_2$$

TABLE 1

| Conditions | Film (Sheet) Speed | Roller No. | Roller Speed (Surface Speed) | Abrasion Standard | Abrasive Material |
|---|---|---|---|---|---|
| No. 1 | 10 m/min | 8 | 100 m/min | AS180 | Alumina |
|  |  | 9 | " | " | " |
|  |  | 10 | " | AS500 | " |
|  |  | 11 | " | " | " |
| No. 2 | 5 m/min | 8 | 80 m/min | AS180 | " |
|  |  | 9 | " | " | " |
|  |  | 10 | 100 m/min | AS320 | " |
|  |  | 11 | " | " | " |

EXAMPLE 2

Spherical silica gel having a specific gravity of 0.45, a surface area of 400 m²/g and a pH of a 5% suspension thereof of 7 and an average pore diameter of 90 Å and containing at least 65% of particles of a diameter of 20–50μ was treated with 2% solution of a fluorine-containing water-repellent emulsion in such a manner that the water-repellent was attached thereto in an amount of 7%. Thus treated silica gel beads were kneaded in a medium density polyethylene having a density of 0.922, a melt index of 0.7 and a melting point of 120° C. in such an amount that the weight fraction thereof was 10%. The mixture was shaped into films of a thickness of 25μ by the T-die method.

The films were abraded under abrasion conditions No. 1 in above Table 1 to obtain a porous sheet having the following properties:
Vapor permeation: 1.5 (g/100 cm²)
Resistance to water pressure: 1.3 (m/cm²)
Strength ratio (MD/CD): 1.3/1.0
(Note):
CD: Strength in cross direction
MD: Strength in machine direction

EXAMPLE 3

Broken pieces of silica-alumina gel having an average particle diameter of 30–40μ, a specific gravity of 0.55, a surface area of 400 m²/g, a pH of a 10% suspension thereof of 9.5 and an average pore diameter of 120 Å were kneaded in a polypropylene having a density of 0.90, a melt index of 1.2 and a melting point of 160° C. in such a manner that the weight fraction thereof was 10%. Films of a thickness of 30μ were prepared therefrom by the inflation method.

The films were abraded under abrasion conditions No. 2 in above Table 1 and then treated with 30% solution of silicone emulsion in such a manner that the water-repellent was attached thereto in an amount of 7%. As a result, porous sheets having the following properties were obtained.
Vapor permeation: 1.3 (g/100 cm²)
Resistance to water pressure: 1.2 (m/cm²)
Strength ratio (MD/CD): 1.0/1.1

EXAMPLE 4

A polypropylene having a density of 0.90, a melt index of 1.2 and a melting point of 160° C. was blended with an ethylene/α-olefin copolymer elastomer (modifier for blending resin) in a ratio of 70/30. Then, zeolite having a particle diameter of 15–40μ, a bulk density of 0.36 g/ml., and a pore volume of 1.4 cm²/g was incorporated therein in an amount of 20% weight fraction based on the resin blend. Films of a thickness of 25μ were prepared therefrom by the inflation method. The resulting films were abraded under abrasion conditions No. 2 in Table 1 and then treated with 2% solution of a fluorine-containing water-repellent emulsion in such a manner that the water repellent was attached thereto in an amount of 5%. As a result, porous sheets having the following properties were obtained.
Vapor permeation: 1.5 (g/100 cm²)
Resistance to water pressure: 1.0 (m/cm²)
Strength ratio (MD/CD): 1.2/1.0

EXAMPLE 5

Polystyrene beads having an average particle diameter of 30μ were kneaded in a low density polyethylene having a weight-average molecular weight of 9,300, a melt index of 5 and a melting point of 109° C. in such an amount that the weight fraction of the former was 15%. Films of a thickness of 30μ were prepared therefrom by the T-die method. The resulting films were abraded under abrasion conditions No. 1 in Table 1 and then under abrasion conditions No. 2 in the same table to obtain porous sheets of the following properties: In this case, the water-repelling treatment was unnecessary, since the polystyrene beads per se were water-repellent.
Vapor permeation: 0.8 (g/100 cm²)
Resistance to water pressure: 1.8 (m/cm²)
Strength ratio (MD/CD): 1.05/1.0

EXAMPLE 6

For examining the strength ratio, a film of 30 g/m² comprising a high density polyethylene and calcium carbonate and having a film thickness of 40μ prepared by stretching method and a film of 25 g/m² comprising the same components as above and having a film thickness of 25μ were abraded and forces required for tearing them in machine direction and cross direction were measured to obtain the following results:

| | Tearing stress | | |
|---|---|---|---|
| | MD | CD | MD/CD |
| Stretching process | 50.2 g | 29.3 g | 1.7 |
| Process of the invention | 40 | 32 | 1.3 |

The embodiments of the invention in which an exclusive property or privilege is claimed are defined as follows:

1. A liquid-impermeable, vapor-permeable, thin, flexible, porous sheet made from a composition comprising a blend of thermoplastic resin and solid filler particles, said thermoplastic resin forming a matrix in which said solid filler particles are dispersed, said solid filler particles extending to the opposite surfaces of said sheet, said thermoplastic resin matrix being spaced from the surfaces of said solid filler particles thereby to provide apertures surrounding said solid filler particles, the portions of said thermoplastic matrix on the opposite surfaces of said sheet that overlie the outermost portions of said solid filler particles having been removed by abrasion or buffing so that said outermost portions of said solid filler particles are uncovered and exposed and said apertures form passages that extend between and penetrate through said opposite surfaces of said sheet, said passages being of a small size so that liquid cannot substantially permeate through said sheet and vapor can permeate through said sheet.

2. A porous sheet as claimed in claim 1 containing from about 5 to 40 wt.% of said solid filler particles, based on the weight of said sheet.

3. A porous sheet as claimed in claim 1 in which said thermoplastic resin is selected from the group consisting of polyethylene, nylon and polyester resin.

4. A porous sheet as claimed in claim 1 in which said filler particles are made of a material selected from the group consisting of glass beads, polystyrene, zeolite, silica alumina gel, calcium carbonate, barium sulfate, pearlite, diatomaceous earth and white carbon.

5. A porous sheet as claimed in claim 1, wherein said filler particles have a substantially different coefficient of thermal expansion than said thermoplastic resin.

6. A porous sheet as claimed in claim 5, wherein said sheet is prepared by molding said composition wherein said thermoplastic resin is in a molten state and then cooling said sheet, whereby said apertures form around the outer surfaces of said particles, and then subjecting said cooled sheet to said abrasion or buffing.

7. A porous sheet as claimed in claim 1 wherein the thickness of said solid filler particles is at least about as large as the thickness of said thermoplastic matrix between said solid filler particles.

8. A porous sheet according to claim 1 wherein said solid filler particles have a diameter in the range of from 1 micron to the sum of the thickness of said sheet plus 60 microns.

9. A porous sheet according to claim 1 wherein the outer surfaces of said solid filler particles have been treated so as to impart water-repellency thereto.

10. A process for manufacturing a liquid-impermeable, vapor-permeable, thin, flexible, porous sheet, which comprises the steps of: blending thermoplastic resin and solid filler particles to form a molding composition; molding said composition to form a thin, flexible sheet wherein said thermoplastic resin forms a matrix in which said filler particles are dispersed with said solid filler particles extending to the opposite surfaces of said sheet and with said thermoplastic resin matrix being spaced from the surfaces of said solid filler particles thereby to provide apertures surrounding said solid filler particles; then abrading or buffing the opposite surfaces of said sheet to remove the portions of said thermoplastic matrix on the opposite surfaces of said sheet that overlie the outermost portions of said solid filler particles so that said outermost portions of said solid filler particles are uncovered and exposed and said apertures form passages that extend between and penetrate through said opposite surfaces of said sheet, said passages being of a small size so that liquid cannot substantially permeate through said sheet and vapor can permeate through said sheet.

* * * * *